United States Patent [19]
Kim

[11] Patent Number: 5,991,657
[45] Date of Patent: Nov. 23, 1999

[54] ATRIAL CARDIOVERTER WITH WINDOW BASED ATRIAL TACHYARRHYTHMIA DETECTION SYSTEM AND METHOD

[75] Inventor: Jaeho Kim, Redmond, Wash.

[73] Assignee: Cardiac Pacemakers, Inc., St. Paul, Minn.

[21] Appl. No.: 09/130,385

[22] Filed: Aug. 6, 1998

[51] Int. Cl.[6] .................................................. A61N 1/39
[52] U.S. Cl. ................................................................ 607/5
[58] Field of Search .......................................... 607/4, 5

[56] References Cited

U.S. PATENT DOCUMENTS 5,755,736  5/1998  Gillberg et al. .............................. 607/4
5,853,426  12/1998  Shieh .......................................... 607/5

Primary Examiner—Scott M. Getzow
Attorney, Agent, or Firm—Foley & Lardner

[57] ABSTRACT

There is disclosed an implantable atrial cardioverter for delivering therapy to atria of a human heart if an atrial tachyarrhythmia is present. The cardioverter includes a first sense channel for sensing atrial heart activity within the right atrium of the heart for providing an atrial electrogram having a plurality of cardiac cycles and a second sense channel for sensing ventricular activity of the heart to provide a ventricular electrogram. The cardioverter further includes an atrial tachyarrhythmia detector including a detection window stage responsive to at least the ventricular electrogram to identify for each cardiac cycle of the atrial electrogram, a detection window period free of any heart activity other than spontaneous atrial heart activity, an A wave detector for identifying A waves occurring during each detection window period means for determining atrial cycle lengths between the identified A waves, and a decision stage responsive to the determined atrial cycle lengths for determining if an atrial tachyarrhythmia is present. A cardioverting stage delivers therapy to the atria if an atrial tachyarrhythmia is present.

17 Claims, 1 Drawing Sheet

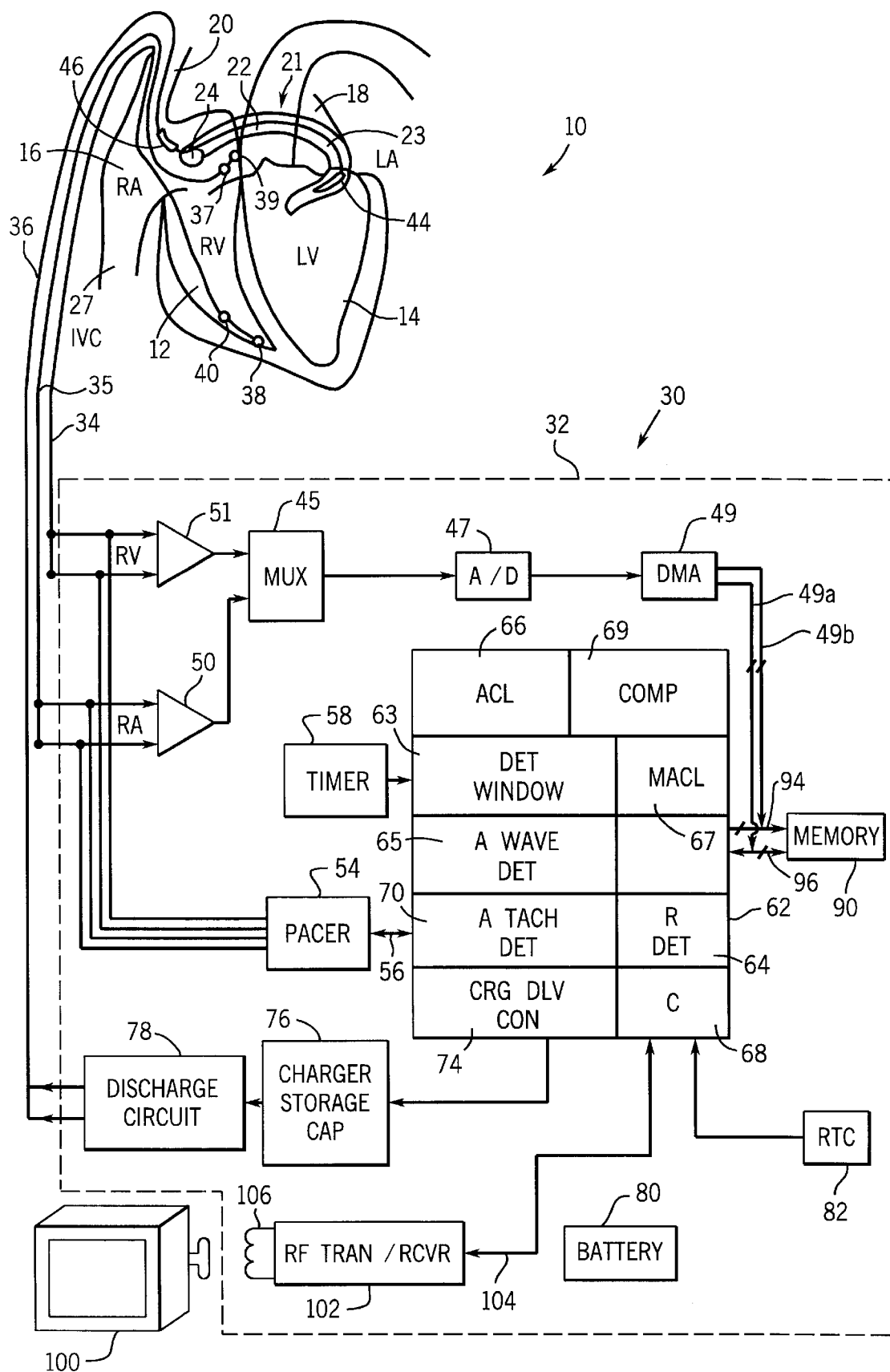

ATRIAL CARDIOVERTER WITH WINDOW BASED ATRIAL TACHYARRHYTHMIA DETECTION SYSTEM AND METHOD

BACKGROUND OF THE INVENTION

The present invention generally relates to an atrial cardioverter having a system for detecting atrial tachyarrhythmias of a heart. The present invention is more particularly directed to such a system and method which detects atrial tachyarrhythmias with a high degree of specificity even though the heart may be paced at the same time in a dual or single chamber mode.

Atrial tachyarrhythmias are common cardiac arrhythmias and are evidenced by very fast atrial rates. They are generally classified as either atrial flutter which is also generally associated with a fast and substantially constant ventricular rate or atrial fibrillation which is also generally associated with a fast but variable ventricular rate.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. Because patients afflicted with atrial fibrillation generally experience rapid and irregular beating of the heart they may even experience dizziness as a result of reduced cardiac output.

Atrial tachyarrhythmia occurs suddenly, and many times can only be corrected by discharging electrical energy into the atria of the heart of the patient. This treatment is preferably synchronized to a detected R wave of the heart in order to avoid shocking the atria during the T wave or vulnerable period of the heart. The amount of energy which may be required to successfully cardiovert the atria can be as low as one joule and as high as six joules. In the cases of atrial fibrillation, energy of about two to six joules is often effective to cardiovert atrial fibrillation back to normal sinus rhythm (NSR).

Implantable atrial cardioverters or defibrillators are known which detect the presence of an atrial tachyarrhythmia and provide a single cardioverting pulse of electrical energy to the atria when atrial fibrillation is detected. Atrial tachyarrhythmia detection may be initiated at spaced apart times with such devices to conserve battery power as disclosed, for example, in U.S. Pat. No. 5,464,432. Alternatively, such devices may provide continuous monitoring of heart activity to activate more specific atrial tachyarrhythmia detections when the monitored activity indicates a probability of an atrial tachyarrhythmia.

One such implantable device is disclosed in U.S. Pat. No. 5,282,837. As disclosed in that patent, ventricular activity is continuously monitored. When the ventricular rate and/or ventricular rate variability reach a certain level, an atrial tachyarrhythmia is suspected and a more robust and higher battery energy consumption algorithm for atrial fibrillation detection is initiated and implemented with a microprocessor.

Whether continuous monitoring or intermittent monitoring is used to initiate atrial tachyarrhythmia detection, such detection must be highly specific to an atrial tachyarrhythmia. The reason for this is that patients will normally be conscious during the atrial tachyarrhythmia therapy. While highly specific atrial tachyarrhythmia detection algorithms are known, these algorithms have not been called upon to detect atrial tachyarrhythmias in the presence of single or dual chamber pacing. Such pacing from an atrial cardioverter or defibrillator has recently received great attention and support as a way to adapt an atrial cardioverter/defibrillator for a greater number of patients.

The present invention provides such specific atrial tachyarrhythmia detecting notwithstanding the presence of single or dual chamber pacing. More specifically, the present invention first relies upon atrial activity sensing within the right atrium to reduce far field sensing as much as possible. Further, detection windows are established whereby only heart activity free of any heart activity other than spontaneous atrial heart activity is relied upon in detecting an atrial tachyarrhythmia.

SUMMARY OF THE INVENTION

The invention provides an implantable atrial cardioverter for delivering therapy to atria of a human heart if an atrial tachyarrhythmia is present. The cardioverter includes a first sensor for sensing atrial heart activity within the right atrium of the heart for providing an atrial electrogram having a plurality of cardiac cycles, and a second sensor for sensing ventricular activity of the heart to provide a ventricular electrogram. The atrial cardioverter further includes an atrial tachyarrhythmia detector including detection window means responsive to at least the ventricular electrogram to identify, for each cardiac cycle of the atrial electrogram, a detection window period free of any heart activity other than spontaneous atrial heart activity, an A wave detector for identifying A waves occurring during each detection window period, means for determining atrial cycle lengths between the identified A waves, and decision means responsive to the determined atrial cycle lengths for determining if an atrial tachyarrhythmia is present. The atrial cardioverter further includes a cardioverting stage responsive to the atrial tachyarrhythmia detector for delivering therapy to the atria if an atrial tachyarrhythmia is present.

The present invention further provides a method of delivering therapy to atria of a human heart if an atrial tachyarrhythmia is present. The method includes the steps of sensing atrial heart activity within the right atrium of the heart to provide an atrial electrogram having a plurality of cardiac cycles, sensing ventricular activity of the heart to provide a ventricular electrogram, and responsive to at least the ventricular electrogram, identifying, for each cardiac cycle of the atrial electrogram, a detection window period free of any heart activity other than spontaneous atrial heart activity. The method further includes the steps of identifying A waves occurring during each detection window period, determining atrial cycle lengths between the identified A waves responsive to the determined atrial cycles lengths, determining if an atrial tachyarrhythmia is present, and delivering cardioverting therapy to the atria if an atrial tachyarrhythmia is present.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a schematic block diagram of a fully implantable atrial cardioverter/defibrillator embodying the present invention.

DETAILED DESCRIPTION OF THE PREFERRED EMBODIMENT

Prior to referring to FIG. 1, a general description of a typical or normal cardiac cycle may be helpful in understanding the operation and various aspects of the present invention. The beginning of a cardiac cycle in normal sinus rhythm is initiated by a P wave which is normally a small positive wave. The P wave induces depolarization of the atria of the heart. Following the P wave there is a cardiac cycle portion which is substantially constant having a time duration on the order of, for example, 120 milliseconds. As a precaution, and to avoid potential confusion, the term "A wave" shall be used herein to denote atrial activity including P waves satisfying certain amplitude or threshold requirements.

The QRS complex of the cardiac cycle then normally occurs after the substantially constant portion. The dominating feature of the QRS complex is the ventricular activation, or R wave, which is a rapid positive or negative deflection. The P wave generally has an amplitude greater than any other wave of the cardiac cycle and is characterized by a rapid deviation from and return toward baseline. The R wave is the depolarization of the ventricles. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds.

Referring now to FIG. 1, it illustrates a fully implantable atrial defibrillator 30 embodying the present invention shown in association with a schematically illustrated human heart 10. The portions of the heart 10 illustrated in the sole FIGURE are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 27.

The atrial defibrillator 30 generally includes an enclosure 32 for hermetically sealing the internal circuit elements of the atrial defibrillator to be described hereinafter, a ventricular endocardial or first lead 34, a right atrial endocardial or second lead 35 and an intravascular or third lead 36. The enclosure 32 and leads 34, 35, and 36 are arranged to be implanted beneath the skin of a patient so as to render the atrial defibrillator 30 fully implantable.

The intravascular lead 36 generally includes a first or tip electrode 44 and a second proximal electrode 46. As illustrated, the lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 and the second electrode 46 further provide for the delivery of cardioverting or defibrillating electrical energy to the atria. The electrodes 44 and 46 are preferably elongated cardioverting electrodes.

The first lead 34 preferably comprises a ventricular endocardial lead having bi-polar pair electrodes 38 and 40 arranged for establishing electrical contact with the right ventricle 12 of the heart 10. The electrodes 38 and 40 permit bi-polar sensing of ventricular activations in the right ventricle and pacing in the right ventricle. As illustrated, the lead 34 is fed through the superior vena cava 20, into the right atrium 16, and then into the right ventricle 12.

The second lead 35 preferably comprises a right atrial endocardial lead having bi-polar pair electrodes 37 and 39. Electrode 39 preferably is a helical screw-in coil for both providing fixation of the lead 35, as known in the art, and establishing electrical contact with the right atrium 16 of the heart 10. The electrodes 37 and 39 permit localized bi-polar sensing of heart activity within the right atrium. As illustrated, the lead 35 is fed through the superior vena cava 20 and into the right atrium 16.

Within the enclosure 32, the atrial defibrillator 30 includes a first sense amplifier 50, and a second sense amplifier 52. The first sense amplifier 50 forms an RA channel to provide an atrial electrogram of the sensed right atrial heart activity at its output which is coupled to an input of a multiplexer 45. Because the electrodes 37 and 39 are closely spaced within the right atrium to sensed localized atrial heart activity, far field sensing is substantially reduced. As will be seen hereinafter, it is this right atrial electrogram produced by the electrodes 37 and 39 and sense amplifier 50 which is utilized for detecting an atrial tachyarrhythmia in accordance with this preferred embodiment of the present invention.

The second sense amplifier 52 forms an RV channel to provide an electrogram of the sensed right ventricular heart activity at its output which is coupled to another input of the multiplexer 45. Each of the sense amplifiers 50 and 52 may include a differentiating filter so that the electrograms which they provide are differentiated electrogram signals.

The enclosure 32 of the atrial defibrillator 30 further includes a microprocessor 62. The microprocessor 62 is preferably implemented in accordance with this embodiment of the present invention to result in a plurality of functional stages. The stages include an atrial tachyarrhythmia detector 70 and a charge and energy delivery control stage 74. The atrial tachyarrhythmia detector includes a detection window stage 63, an R wave detection stage 64, an A wave detection stage 65, an atrial cycle length (ACL) stage 66, a mean atrial cycle length (MACL) stage 67, a counter 68, and a comparison stage 69.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or receives programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from the external controller 100 and for transmitting data to the external controller 100. One preferred communication system is disclosed in copending U.S. Pat. No. 5,342,408 which issued on Aug. 30, 1994 for "Telemetry System for an Implantable Cardiac Device," which patent is assigned to the assignee of the present invention and incorporated herein by reference.

The atrial defibrillator 30 further includes an analog to digital converter 47 and a direct memory access controller (DMA) 49. The analog to digital converter 47 has an input coupled to the output of the multiplexer 45 for receiving the electrogram signals generated by the sense amplifiers 50 and 52. During a data acquisition, which initiates an atrial tachyarrhythmia detection, the analog to digital converter 47 converts the electrogram signals into digital data. The digital data is received by the DMA 49 and conveys the digital data to memory 90 over a data bus 49a for storage in memory at predetermined locations selected by the DMA 49 over an address bus 49b. The electrogram signals thus stored in digital form representing activity of the heart are thereafter utilized by the microprocessor to perform atrial tachyarrhythmia detection. More specifically, the atrial tachyarrhythmia detector 70 utilizes the stored data from the RA channel for detecting the presence of atrial fibrillation of the heart.

The atrial cardioverter/defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. The defibrillator 30 further includes a depletable power source 80, such as a lithium battery, for providing power to the electrical components of the atrial defibrillator 30, and a real time clock 82.

A pacer 54 is further provided for providing pacing therapy to the heart. The pacer may be of the type well known in the art initially configurable by the microprocessor over a bi-directional bus 56 into any of the known therapies including single chamber atrial or ventricular pacing, dual chamber pacing, or atrial antitachycardia overdrive pacing. To that end, the pacer is coupled to electrodes 37 and 39 in the right atrium and to electrodes 38 and 40 in the right ventricle. This permits the pacer to both sense in the right atrium and right ventricle to support demand pacing and apply pacing pulses to the right atrium and right ventricle. For reasons to be explained subsequently, whenever the pacer applies a pacing pulse to the right atrium or the right ventricle, it also provides an interrupt to the microprocessor over the bus 56.

To briefly describe the operation of the atrial cardioverter/defibrillator for cardioverting atrial fibrillation of the heart, when an atrial tachyarrhythmia detection is initiated at spaced apart times by timer 58, in accordance with the present invention, the sense amplifiers 50 and 52, the analog to digital converter 47, the multiplexer 45 and the DMA 49 are enabled. A data acquisition is first performed for a data acquisition period of, for example, eight seconds. During the eight second data acquisition period, the electrogram signals from sense amplifiers 50 and 52 are digitized by the analog to digital converter 47 into digital data and the digital data is caused to be stored in the memory 90 by the DMA 49 as previously described.

After the eight second data acquisition period is completed, the atrial tachyarrhythmia detector 70 is enabled and analyzes the stored electrogram data in a manner to be described subsequently. If an atrial tachyarrhythmia is present and the atria are thus in need of cardioversion, the charge delivery control 74 causes the charger and storage capacitor circuit 76 to charge the storage capacitor within the circuit 76 to a selected peak voltage. After the capacitor is charged, another data acquisition is performed and the atrial tachyarrhythmia detector 70 confirms the presence of the atrial tachyarrhythmia. Thereafter, the R wave detector 64 of the microprocessor 62 processes the digital data from the RV channel in real time to detect an R wave to synchronize the delivery of the cardioverting energy when such an R wave is detected, the discharge circuit 78 applies a portion of the stored electrical energy to electrodes 44 and 46 and thus the atria 16 and 18 to cardiovert the atria 16 and 18.

In accordance with a preferred embodiment of the present invention, the atrial tachyarrhythmia detector 70 detects the presence of an atrial tachyarrhythmia with high specificity even if the heart is being paced. For completeness, the following discussion will assume that the pacer 54 is pacing the heart in a dual chamber mode such as the DDD mode.

During the data acquisition, each time the pacer 54 applies a pacing pulse to the heart, it provides an interrupt to the microprocessor over the bus 56. The microprocessor time stamps each such interrupt and stores the time stamps with the stored electrogram data. It further stores the time stamps according to its source as either a ventricular pace time stamp or an atrial pace time stamp.

After the data acquisition is completed, there will be stored in memory 90 electrogram data from both the sense amplifier 50 (atrial channel) and the sense amplifier 52 (ventricular channel) representing a plurality of cardiac cycles which occurred during the data acquisition period. The R Wave detector 64 first analyzes the ventricular electrogram data to identify intrinsic R waves. For each spontaneous or intrinsic R wave, it notes the time when the R wave began and the time when the R wave ended. Next, the detection window stage 63 identifies for each recorded cardiac cycle a detection window period free of any heart activity other than spontaneous atrial heart activity. Depending upon the nature of the cardiac cycle, the detection window period is defined as beginning at the end of an intrinsic R wave or after the end of a blanking period following each atrial or ventricular pacing pulse. The blanking period, which may be 40 milliseconds, for example, assures that the driven A wave or R wave has completed before the detection window period is considered to be started. The detection window period ends at or slightly before the start of a next intrinsic R wave, at delivery of an immediately succeeding ventricular pacing pulse or at delivery of an immediately succeeding atrial pacing pulse. By identifying the detection window periods in this manner, the detection window stage 63 assures that when the RA channel electrogram data is analyzed during the identified detection window periods, the analyzed data will be free of any heart activity data other than spontaneous or intrinsic atrial heart activity data.

Next, the A wave detector 65 analyzes the RA channel electrogram data which occurred during only the detection window periods to identify each A wave. Thereafter, the ACL stage 66 determines, for each cardiac cycle, the atrial cycle length or duration between successive A waves. The ACL stage 66 will do this only if there was more than one A wave during the given detection window period.

The number of determined atrial cycle lengths are counted by the counter 68. When a required number, such as twelve, for example, of atrial cycle lengths have been determined and counted, the MACL stage 67 then determines a mean atrial cycle length from the determined atrial cycle lengths.

Once the mean atrial cycle length is determined, a decision is made if an atrial tachyarrhythmia is present. To that end, the comparison stage 69 compares the determined mean atrial cycle length to a preset value, for example, 280 milliseconds. If the mean atrial cycle length is less than the preset value, an atrial tachyarrhythmia is deemed to be present and therapy, as previously described, is initiated. However, if the mean atrial cycle length is equal to or greater than the preset value, an atrial tachyarrhythmia is not deemed to be present and therapy is inhibited or not initiated.

From the foregoing, it can be seen that the present invention provides an atrial cardioverter having an atrial tachyarrhythmia detector capable of detecting an atrial tachyarrhythmia with a high specificity even though the heart is being paced. This is made possible by the identification of a detection window period for each analyzed cardiac cycle of the RA channel electrogram which is free of an heart activity other than spontaneous or intrinsic atrial heart activity. Such specificity is further advanced by the sensing of atrial activity for analysis within the right atrium using a closely spaced bi-polar pair of sensing electrodes.

While a particular embodiment of the present invention has been shown and described, modifications may be made. It is therefore intended in the appended claims to cover all such changes and modifications which fall within the true spirit and scope of the invention.

What is claimed is:

1. An implantable atrial cardioverter for delivering therapy to atria of a human heart if an atrial tachyarrhythmia is present, the cardioverter comprising:

first sensing means for sensing atrial heart activity within the right atrium of the heart for providing an atrial electrogram having a plurality of cardiac cycles;

second sensing means for sensing ventricular activity of the heart to provide a ventricular electrogram;

an atrial tachyarrhythmia detector including detection window means responsive to at least the ventricular electrogram to identify for each cardiac cycle of the atrial electrogram, a detection window period free of any heart activity other than spontaneous atrial heart activity, an A wave detector for identifying A waves occurring during each detection window period means for determining atrial cycle lengths between the identified A waves, and decision means responsive to the determined atrial cycle lengths for determining if an atrial tachyarrhythmia is present; and cardioverting means responsive to the atrial tachyarrhythmia detector for delivering therapy to the atria of an atrial tachyarrhythmia is present.

2. A cardioverter as defined in claim 1 wherein the first sensing means includes a pair of electrodes adapted for implantation in the right atrium.

3. A cardioverter as defined in claim 1 wherein the second sensing means includes a pair of electrodes adapted for implantation in the right ventricle.

4. A cardioverter as defined in claim 1 wherein the means for determining atrial cycle lengths only determines an atrial cycle length for a given detection window if more than one A wave occurs in the given detection window.

5. A cardioverter as defined in claim 1 further including means for determining a mean atrial cycle length and wherein the decision means is responsive to the mean atrial cycle length for determining if an atrial tachyarrhythmia is present.

6. A cardioverter as defined in claim 5 wherein the means for determining a mean atrial cycle length only determines a mean atrial cycle length if at least a predetermined number of atrial cycle lengths have been determined.

7. A cardioverter as defined in claim 1 further including a pacer for applying pacing pulses to the atria and/or the ventricles to produce non-spontaneous heart activity including driven R waves and driven A waves.

8. A cardioverter as defined in claim 7 wherein each detection window begins after a spontaneous R wave or after a driven A wave or R wave and ends at or before the start of a next spontaneous R wave, at delivery of an immediately succeeding ventricular pacing pulse, or at delivery of an immediately succeeding atrial pacing pulse.

9. A cardioverter as defined in claim 1 further including a memory, wherein the atrial and ventricular electrograms are stored in the memory as digital data, and wherein the atrial tachyarrhythmia detector processes the digital data to determine if an atrial tachyarrhythmia is present.

10. A method of delivering therapy to atria of a human heart if an atrial tachyarrhythmia is present the method including the steps of:

sensing atrial heart activity within the right atrium of the heart to provide an atrial electrogram having a plurality of cardiac cycles;

sensing ventricular activity of the heart to provide a ventricular electrogram;

responsive to at least the ventricular electrogram, identifying, for each cardiac cycle of the atrial electrogram, a detection window period free of any heart activity other than spontaneous atrial heart activity;

identifying A waves occurring during each detection window period;

determining atrial cycle lengths between the identified A waves;

responsive to the determined atrial cycle lengths, determining if an atrial tachyarrhythmia is present, and delivering cardioverting therapy to the atria if an atrial tachyarrhythmia is present.

11. A method as defined in claim 10 including the further step of implanting a pair of electrodes in the right atrium.

12. A method as defined in claim 10 including the further step of implanting a pair of electrodes in the right ventricle.

13. A method as defined in claim 10 wherein the atrial cycle length determining steps includes only determining an atrial cycle length for a given detection window if more than one A wave occurs in the given detection window.

14. A method as defined in claim 10 including the further step of determining a mean atrial cycle length and wherein the last recited determining step includes determining if an atrial tachyarrhythmia is present responsive to the mean atrial cycle length.

15. A method as defined in claim 14 wherein the step for determining a mean atrial cycle length includes only determining a mean atrial cycle length of at least a predetermined number of atrial cycle lengths have been determined.

16. A method as defined in claim 10 wherein a pacer applies pacing pulses to the atria and/or the ventricles to produce non-spontaneous heart activity including driven R waves and driven A waves, and wherein the detection window identifying step includes beginning each detection window after a spontaneous R wave or after a driven R wave and ending each detection window at or before the start of a next spontaneous R wave, at delivery of an immediately succeeding ventricular pacing pulse, or at delivery of an immediately succeeding atrial pacing pulse.

17. A method as defined in claim 10 further including the steps of storing the atrial and ventricular electrograms in a memory as digital data, and processing the digital data to determine if an atrial tachyarrhythmia is present.

* * * * *